United States Patent
Nault-Richter (10) Patent No.: US 7,954,196 B1
(45) Date of Patent: Jun. 7, 2011

(54) MINI MULTITASK BRUSH

(76) Inventor: Michele Rene Nault-Richter, Missoula, MT (US)

( * ) Notice: Subject to any disclaimer, the term of this patent is extended or adjusted under 35 U.S.C. 154(b) by 664 days.

(21) Appl. No.: 12/075,758

(22) Filed: Mar. 14, 2008

(51) Int. Cl.
*A46B 5/02* (2006.01)
*A46B 7/02* (2006.01)
*A46B 7/04* (2006.01)
*A46B 9/04* (2006.01)

(52) U.S. Cl. ....... 15/167.1; 15/143.1; 15/172; 15/176.1; 15/184; 132/311

(58) Field of Classification Search ........... 15/143.1, 15/167.1, 172, 176.1, 176.6, 184; 132/308, 132/310, 311
See application file for complete search history.

(56) References Cited

U.S. PATENT DOCUMENTS

| | | | | |
|---|---|---|---|---|
| 1,063,523 | A | * | 6/1913 | Farrar .................. 15/167.1 |
| 1,847,495 | A | * | 3/1932 | Priest .................... 132/309 |
| 1,859,129 | A | * | 5/1932 | Costenbader ........... 15/172 |
| 1,874,467 | A | * | 8/1932 | Doll ...................... 15/167.1 |
| D107,228 | S | | 11/1937 | Goodman |
| 2,679,657 | A | * | 6/1954 | Krueger ................. 15/172 |
| 4,209,871 | A | * | 7/1980 | Ernest et al. .......... 15/167.1 |
| 4,330,896 | A | | 5/1982 | Booth |
| 4,598,437 | A | * | 7/1986 | Ernest et al. .......... 15/176.1 |
| 4,654,922 | A | | 4/1987 | Chen |
| 5,046,212 | A | | 9/1991 | O'Conke |
| 5,058,230 | A | * | 10/1991 | Hodosh et al. ........ 15/167.1 |
| 5,242,301 | A | | 9/1993 | Hickey |
| 5,339,482 | A | * | 8/1994 | Desimone et al. .... 15/167.1 |
| 5,400,457 | A | | 3/1995 | Ridgley |
| 5,491,866 | A | | 2/1996 | Simonds |
| 5,517,713 | A | | 5/1996 | Hadcock |
| 5,581,838 | A | | 12/1996 | Rocco |
| 5,749,381 | A | | 5/1998 | Butler |
| 5,766,008 | A | | 6/1998 | Hughes |
| 5,815,875 | A | | 10/1998 | Yamada |
| 5,850,659 | A | | 12/1998 | Butler |
| 5,862,558 | A | | 1/1999 | Hilfinger |
| 5,934,295 | A | | 8/1999 | Gekhter |
| RE36,407 | E | | 11/1999 | Rocco |
| 5,974,613 | A | | 11/1999 | Herzog |
| 6,018,838 | A | | 2/2000 | Nowack |
| D421,841 | S | | 3/2000 | Achepohl |
| 6,161,244 | A | | 12/2000 | Jeannet |
| 6,219,874 | B1 | | 4/2001 | Van Gelder |
| 6,260,227 | B1 | | 7/2001 | Fulop |
| 6,345,406 | B1 | | 2/2002 | Dodd |
| 6,374,450 | B1 | | 4/2002 | Aoyama |

(Continued)

OTHER PUBLICATIONS

Wikipedia, the free encyclopedia, Mar. 2006, Wikipedia Foundation, Inc., www.wikipedia.org.

(Continued)

*Primary Examiner* — Mark Spisich (57) ABSTRACT

A brush small in diameter consisting of stiff bristles of 0.014 inch nylon filaments bundled in 50 nylon filaments glued within a plastic shank. Stiff, short 4 mm, flat even ended bristles are equal in length to form a substantially planar cleaning surface. The small diameter allows for improved dental hygiene via clearance in tight areas such as under orthodontic arch wires and other dental prostheses along with maintaining hygiene in normal and healthy oral cavities. The bristles are capable of fluoride and antibacterial mouthrinse transfer to treat sensitivity, decalcification and inflamed or infected gumline areas. The ergonomical handle has an angled neck, over molded soft grips and additional, replaceable heads are stored inside the hollow handle. The head rotates into multiple angles. Primary embodiment is manual, but other embodiments may allow for mechanical applications that include agitating or reciprocating articulation powered by a motor.

1 Claim, 9 Drawing Sheets

U.S. PATENT DOCUMENTS

| | | |
|---|---|---|
| 6,385,808 B1 | 5/2002 | Yamada |
| 6,446,640 B1 | 9/2002 | Gekhter |
| 6,550,095 B2 | 4/2003 | Hawkins |
| 6,601,272 B2 | 8/2003 | Stvartak |
| 6,775,875 B2 | 8/2004 | Ornelas |
| 7,039,984 B1 | 5/2006 | Watanabe |
| 7,047,591 B2 | 5/2006 | Hohlbein |
| 2003/0019062 A1* | 1/2003 | Florence ............ 15/167.1 |
| 2003/0056311 A1 | 3/2003 | Broecker |
| 2004/0025272 A1 | 2/2004 | Stvartak |
| 2006/0075588 A1 | 4/2006 | Amador |

OTHER PUBLICATIONS

Wilkins, Esther M., Clinical Practice of the Dental Hygienist, Lea and Febiger, 600 Washington Square, Philadelphia, PA 19106, U.S.A.

* cited by examiner

MINI MULTITASK BRUSH

FIELD OF THE INVENTION

The present invention relates to an oral hygiene brush and, more particularly, to an oral hygiene brush mounted on a specialized handle. The brush is designed to be useful for personal or professional tooth cleaning. Orthodontic appliances present a unique cleaning challenge. The present invention has specific utility for cleaning dental appliances and the teeth surrounding the appliances. The present invention will also have utility in the cleaning of irregularly positioned teeth. The present invention will have further utility in cleaning around a dental bridge, a partial plate, dental implants, or other dental prostheses. The brush provides a complement or alternative to cleaning apparatuses such as the Perio-aid or floss threaders. The present invention includes a handle design with a curved shape to fit better in the hand for comfort and grip. The handle has over molded soft grip inserts for softer hand gripping comfort. According to the present invention, the bristles of the brush should be located in an axial position from the handle. The present invention will have utility in transfer and delivery of fluoride application to sensitive root and decalcified areas, and delivery of antibacterial mouthwash to inflamed and infected gum areas. The bristles are intended to be of equal length so that they will form a substantially planar cleaning surface. This is specifically advantageous over prior art which calls for outside bristles to be shorter than inside bristles, thus creating an angular formation to cleaning surface of the brush head. The overall length of the brush bristles of the present invention is shorter than similarly marketed brushes. The brush bristles of the present invention are of high stiffness and density thus creating a smaller diameter head assembly which is important for clearance to tight areas. The head of the present invention is removable and rotatable. The head may be locked into position at multiple angles. This feature specifically eliminates the need for a double headed brush or double-bend handle, as is required by other dental cleaning implements. Replacement or additional heads may be stored in the handle of the present invention. The primary embodiment of the present invention calls for a manual brush. However, other embodiments may allow for mechanical applications including agitating or reciprocating articulation powered by a motor.

BACKGROUND OF THE INVENTION

Dental plaque is a yellowish bio-film that builds up on the teeth, orthodontic braces, and other dental prostheses. The microorganisms that form the bio-film are almost entirely bacteria (mainly streptococcus and anaerobes), with the composition varying by location in the mouth. Bio-films have been found to be involved in a wide variety of microbial infections in the body, by one estimation 80% of all infections (NIH 2002).

Infection processes in which bio-film have been implicated include common problems such as urinary tract infections, catheter infections, middle ear infections, gingivitis, periodontal disease, coating contact lenses, and less common but more lethal processes such as endocarditis, infections in cystic fibrosis and infections of permanent indwelling devices such as joint prosthesis and heart valves. Studies suggest that a relationship between periodontal diseases and a stroke exist. One study found that individuals diagnosed with acute cerebrovascular ischemia were found more likely to have an oral infection.

Gingivitis is the inflammation of the gingiva (gums) around the teeth. Gingivitis may be caused by a build up of plaque and calculus (tartar) due to improper cleaning of teeth, or by injury to the gums from over-vigorous brushing. The condition is generally reversible. Plaque removal is the best way to prevent gingivitis. If gingivitis is not treated, possible problems include periodontitis, an infection or abscess of the gingiva or jaw bone, and trench mouth (bacterial infection and ulceration of the gums).

Periodontal disease is the name for bacterial infections of the gums in the mouth. In most cases this disease is linked to poor oral hygiene. Some people however can have a genetic pre-disposition to the disease. The disease once started can progress more rapidly in people who have diabetes, especially if the diabetes is poorly controlled.

Persons with noninsulin-dependant diabetes mellitus are three times more likely to develop periodontal disease then non diabetics. Evidence exists that a history of chronic periodontal disease can disrupt diabetic control.

Periodontal disease can affect the heart via oral bacteria entering the blood stream, attaching to fatty plaques in the coronary arteries contributing to clot formation.

Endocarditis is an inflammation of the inner layer of the heart, the endocardium. The most common structures involved are heart valves. Bacteria reaches via blood stream causing infection.

Severe periodontal disease in pregnant women can lead to significant increase in the risk of delivering a pre-term, low birth weight baby. A theory is that oral pathogens release toxins that reach the placenta via mother's blood and affects fetal growth.

Scientific studies have found that oral bacteria can reach the lung via aspiration and cause respiratory disease such as pneumonia and exacerbate existing respiratory diseases such as COPD.

A high dental caries rate has been associated with teeth with orthodontic appliances, and severe gingival and periodontal diseases during and following treatment are not unusual. A rigid preventive program for the patient with orthodontic appliance along with a specific plan of instruction, motivation, and supervision are essential. Age of orthodontic patient is a complicating factor due to the fact that most orthodontic patients are preteen and teenage. The incidence of gingivitis is high in this age group. The incidence of periodontal disease increases from early childhood to late teenage. There is a tendency for the gingival tissue to show deviations from normal when plaque increases because of lack of attention to oral health needs.

Puberty is occasionally accompanied by an exaggerated response of the gingiva to local irritation. With orthodontic appliances, the reaction may be compounded, the degree varying from slight to severe enlargement particularly of the inter dental papillae. The tissue may greatly enlarge and cover the bands. Teeth that are irregularly positioned are naturally more susceptible to the retention of deposits and are more difficult to clean. With the severe malocclusions of orthodontic patients, the factor becomes even more significant.

The greater the number of bands on the teeth, the greater increase in bacterial plaque retention.

The problems with appliances happen when plaque, debris, and materia alba are retained. Increased plaque retention leads to increased gingival and periodontal pocket formation.

Self care is difficult even for the patient who tries to maintain oral cleanliness because the appliances are in the way and interfere with the application of the toothbrush and other devices used for plaque control and oral physical therapy.

With such a variety of appliances utilized for orthodontic treatment, it is not possible to specify a single type of brush, the brushing method, or the auxiliary aids that should be selected for each individual patient. Fixed orthodontic appliances may consist of brackets bonded directly to the tooth surfaces after an acid etch procedure. Other appliances are bands cemented around each tooth with brackets attached to the bands to support an arch wire. The selection of plaque control procedures for an individual patient is determined by the severity of the gingivitis or periodontitis, the anatomic features of the gingiva, the position of the teeth, as well as the type and position of the orthodontic appliance.

A dental bridge is a prosthesis used in place of missing teeth. It can be removable or fixed. A removable bridge contains wire hooks that grip the adjoining teeth. A fixed or permanent bridge will span a missing tooth by removing the original surface of the adjacent teeth and cementing to them a common crown shaped to the original surfaces of the two mounting teeth and missing tooth between. The patient must take special care to clean well under this prosthesis.

A dental implant is used in prosthetic dentistry. Osseointegrated implant using titanium allows osteoblasts to grow on and into the rough surfaces of the implanted titanium. Dental implants are not susceptible to caries, but they can develop periodontitis a condition called peri-implantitis when good oral hygiene is not practiced.

A partial can be removed from the mouth and replaced at will. Are made of porcelain, plastic resin, or metal. Because natural teeth are adjacent to the appliance, objectives for cleaning the appliance take on an added significance. Important to remove irritants to the oral tissue and teeth to prevent mouth odors and to improve appearance. A regular toothbrush is recommended for the natural teeth. Although using a regular toothbrush for partial care of a removable appliance is not recommended, when a patient does so, a separate brush is definitely indicated. Brushing the clasps and other metal parts can be destructive to fine toothbrushes. Powered brush is okay for natural teeth, but should not be used in and about the intricate clasps and other parts of a removable appliance because of the danger of catching the brush and damaging the appliance.

Clasp and their connectors are closely adapted to the supporting teeth, and protected internal surface are prone to plaque formation. These difficult to clean areas require special care.

Accumulation of stains and deposits on dentures varies between individuals in a manner similar to that on natural teeth. Phases of deposit formation may be divided as follows: mucin and food debris on the denture surface removed by rinsing or brushing. Denture pellicle and denture plaque. Denture pellicle forms readily after a denture is cleaned. Denture plaque composed of bacteria with a predominance of gram positive cocci and rods in an intermicrobial substance. Plaque serves as a matrix for calculus formation and stain accumulation when the denture is not cleaned. Plaque, particularly older plaque, is tenacious and less easily removed than other soft deposits. Calculus is hard and fixed to the denture surface generally located on the buccal of the maxillary molars and lingual of mandibular anterior region.

Manual and power toothbrushes are instruments used to clean teeth. Toothbrushes are offered with varying textures of bristles, and come in many different sizes and forms. Desirable characteristics of a manual toothbrush designed primarily to promote oral cleanliness are that it conform to individual patient requirements in size, shape, and texture. Be easily and efficiently manipulated. Be readily cleaned and aerated, impervious to moisture. Be durable and inexpensive. Have prime functional properties of flexibility, softness, and diameter of the bristles or filaments, and strength, rigidity and lightness in the handle. Be designed for utility, efficiency and cleanliness. A twist, curve, offset, or angle in the shank may frequently be related to new ideas for advertising appeals, slight deviation may not complicate manipulation or affect control of the brush placement and pressure. Thinner nylon filaments are softer and more resilient. Diameter of soft nylon brushes are 0.006-0.007 inch. Diameter of regular nylon brushes are 0.008 inch for soft, 0.012 inch for medium, 0.014 inch for hard, and 0.016 inch for extra hard.

Automatic, mechanical, and electric brushes are known as powered toothbrushes. The ADA, council on Dental Materials, Instruments and Equipment evaluates and classifies powered brushes as acceptable, or unacceptable. Comparisons have been made in research between the powered and the manual brushes to determine the ability of each type to remove plaque, prevent calculus development and reduce the incidence of gingivitis. Both types have been shown effective when used correctly. The head connected to the shank is detachable from the handle and replaceable. In general, powered brush heads are smaller than manual brushes. They range in size from approximately one quarter to one half inch wide by three quarter inches long. Most powered brushes are multitufted filaments with three or four rows of tufts. The diameter of the available filaments range from 0.005 to 0.007 inch to 0.010 or 0.012 inch. The motion (action) depends on the model. Reciprocating moves back and forth in a line. Arcuate is where filament ends follow an arc as they move up and down. Orbital is circular motion. Vibratory motion. Elliptical is oval motion. Dual motion is more than one of the motions above. Number of strokes/minute can be as low as 1000 cycles/minute for replaceable battery. 3600 oscillations/minute for arcuate model. 2000 complete strokes/minute for rechargeable battery.

Tufted toothbrushes contain multiple bristles. Proxa brushes have a cyndrical or cone shape. Floss threaders pull floss dental through interproximal spaces. Super floss contains a spongy end that can be pulled through interproximal spaces. The perio-aid holds a toothpick. Water jets spray water to remove plaque and food debris. All products can be found in stores, catalogs and the internet. In U.S. Pat. Nos. 4,330,896. 4,654,922. 5,046,212. 5,242,301. 5,400,457. 5,491,866. 5,517,713. 5,581,838. 5,749,381. 5,815,875. 5,850,659. 5,862,558. 5,974,613. 6,018,838. 6,161,244. U.S. Pat. Nos. 6,219,874 B1. 6,260,227. 6,345,406. 6,374,450 B1. 6,385,808 B1. 6,550,095 B2. 6,601,272 B2. 6,775,875 B2. 7,039,984 B1. 7,047,591 B2. US 2003/0056311 A1. US 2004/0025272 A1. US 2006/0075588 A1. Des. 107,228. Re. 36,407. U.S. Pat. Nos. 5,934,295. 6,446,640. D421,841. 5,766,008.

Conventional manual and powered toothbrush heads tend to be too bulky to effectively remove plaque around orthodontic brackets with limited gumline space when individual is in orthodontic braces and other dental prostheses. Orthodontic treatment includes fixed appliances that consist of stainless steel. Removable appliances, headgear, elastic bands and other appliances including expansion appliances and functional appliances. A special orthodontic brush designed with two spaced rows of soft nylon filaments with a third middle row which is shorter can be applied directly over the fixed appliance and used with a short horizontal stroke. This brush is not effective due to the fact that the multi row bristles are too bulky and repeated horizontal strokes may cause gum recession.

Brushes to clean dental bridges tend to be too bulky to use effectively. Proxa brushes are too flimsy to remove gumline plaque around a dental bridge. Floss is intended for interproximal areas, not direct gumline of a dental bridge. Super floss is intended for interproximal use. Perio-aid uses the end of a wooden toothpick that requires to be moistened to soften tip before use. The other end of toothpick may remain too long with sharp edges that scratch the cheek or tongue. Chance of loose bits of wood can be deposited in the sulcus or gingiva. Water jets require water, are messy and may not be real effective removing older plaque. With patients who require antibiotic premedication, bacteremia can occur following the use of oral irrigation, particularly in patients with untreated gingivitis and periodontitis. Abcesses or pericoronal infections can be induced if deep periodontal pockets or tissue flaps covering unerupted or partially erupted third molars. Constant pressure of the water stream over an interdental papilla area may reduce the height of the papilla.

Brushes to clean an implant are too bulky and not site specific because of multiple rows. Tufted brushes contain too many bristles in the head making it impossible to focus on a very small surface. Cylinder of proxa brushes are too flimsy and give way to pressure, and if center of proxa brush is not plastic, can scratch implant.

Brushes for care of partials require two different types of brushes that makes cleaning inconvenient. The need for a separate brush is required because the partial clasps may catch onto the brush and ruin it, or the clasp can be damaged using a big brush.

U.S. Pat. No. 4,330,896, the handle is too narrow, not ergonomical causing hand fatigue. The brush head contains too many rows of bristles making it too bulky to fit in and around small spaces. The bristle ends are uneven making the surface being brushed demanding more strokes.

U.S. Pat. No. 4,654,922, the handle again is too narrow. The brush head is too long, too many rows of bristles and too bulky to fit around and into small limited spaces.

U.S. Pat. No. 5,046,212, the handle again is too narrow. Brush head is too bulky. End opposite of brush head contains a non-removable toothpick, not additional brushes.

It is therefore an object of the invention to provide one brush to perform multiple uses to attain and maintain oral hygiene health.

It is another object of the invention to provide a mini brush that is compact for clearance in tight areas.

It is another object of the invention to provide a mini brush with flat even ended bristles.

It is another object of the invention to provide a mini brush with flat even ended bristles bundled and glued together within a plastic shank.

It is another object of the invention to provide a mini brush with an ergonomical handle.

It is another object of the invention to provide a mini brush with an ergonomical handle with rubber grips.

It is another object of the invention to provide a mini brush with an ergonomical handle with rubber grips that stores additional or replaceable heads.

It is another object of the invention to provide a mini brush with an ergonomical handle with rubber grips that stores additional or replaceable heads and has a rotating head that locks into one of multiple angles.

It is another object of the invention to provide a manual mini brush with flat even ended bristles and ergonomical handle and allow for a mechanical application.

It is another object of the invention to provide a mechanical application that includes agitating or reciprocating articulation powered by a battery operated motor housed within the hollow handle which houses additional and replaceable heads.

SUMMARY OF THE INVENTION

In accordance with the present invention, there is provided a brush attached to an ergonomical handle. For use at home or use at a dental office. Orthodontic appliances are hard to clean. The brush will effectively clean dental appliances and the teeth and gumline surrounding the appliances. The brush will effectively clean irregularly positioned teeth. Will effectively remove plaque around a dental bridge, a partial plate, dental implants, implants with retained overdenture, and will simply remove plaque along gumline of natural healthy teeth where a toothbrush cannot reach. The brush can be used alongside floss, floss threaders or superfloss for complete cleaning of teeth. The brush is an alternative to the perio-aid which relies on toothpicks to clean along the gumline. The brush handle is designed with a curved shape for hand comfort and grip with over molded soft grips for softer hand gripping comfort. The bristles are located in an axial position from the handle. The bristles, are one length to cover more surface. Other product bristles are pointed and require more strokes to clean a surface. The brush bristles are shorter than similar brushes. The brush bristles are stiff and dense so that the brush is small in diameter. This is an important feature for clearance in tight areas. The head rotates and can be locked into one of multiple angles. Multiple angles eliminate the need for a double headed brush or double bend handle that other cleaning devices have. Enticing feature of this invention is that one brush is capable of performing several duties in attaining and maintaining oral health with handle that can be used multiple times and stores additional brushes for use when needed at ones fingertips Primary embodiment is manual, but other embodiments may allow for mechanical applications that include agitating or reciprocating articulation powered by a battery operated motor.

BRIEF DESCRIPTION OF THE DRAWINGS

A complete understanding of the present invention may be obtained by reference to the accompanying drawings, when considered in conjunction with the subsequent, detailed description, in which:

FIG. 10 is a detail view of a conditions that the mini multitask brush can help maintain and keep from getting worse. the gingiva (gum) 26 can recede severely with periodontal disease. after periodontal disease is in control, a condition that you cannot cure, but can maintain oral health with the help of a dental professional and excellent home care. receded gum 43 areas need adequate dental plaque removal to avoid infection and root caries. an embrasure 44 is a wide space in between teeth and develops after periodontal disease due to loss of papilla (gum) in between teeth. the embrasure 44 is wide enough to facilitate the mini multitask brush. furcation 45 of the root happens when the gingiva (gum) 26 has receded far enough to expose the space between a root. this is an indentation that is very difficult to clean. frequent visits with a dental professional and excellent plaque removal are a must;

For purposes of clarity and brevity, like elements and components will bear the same designations and numbering throughout the Figures.

DESCRIPTION OF THE PREFERRED EMBODIMENT

Figure 1:
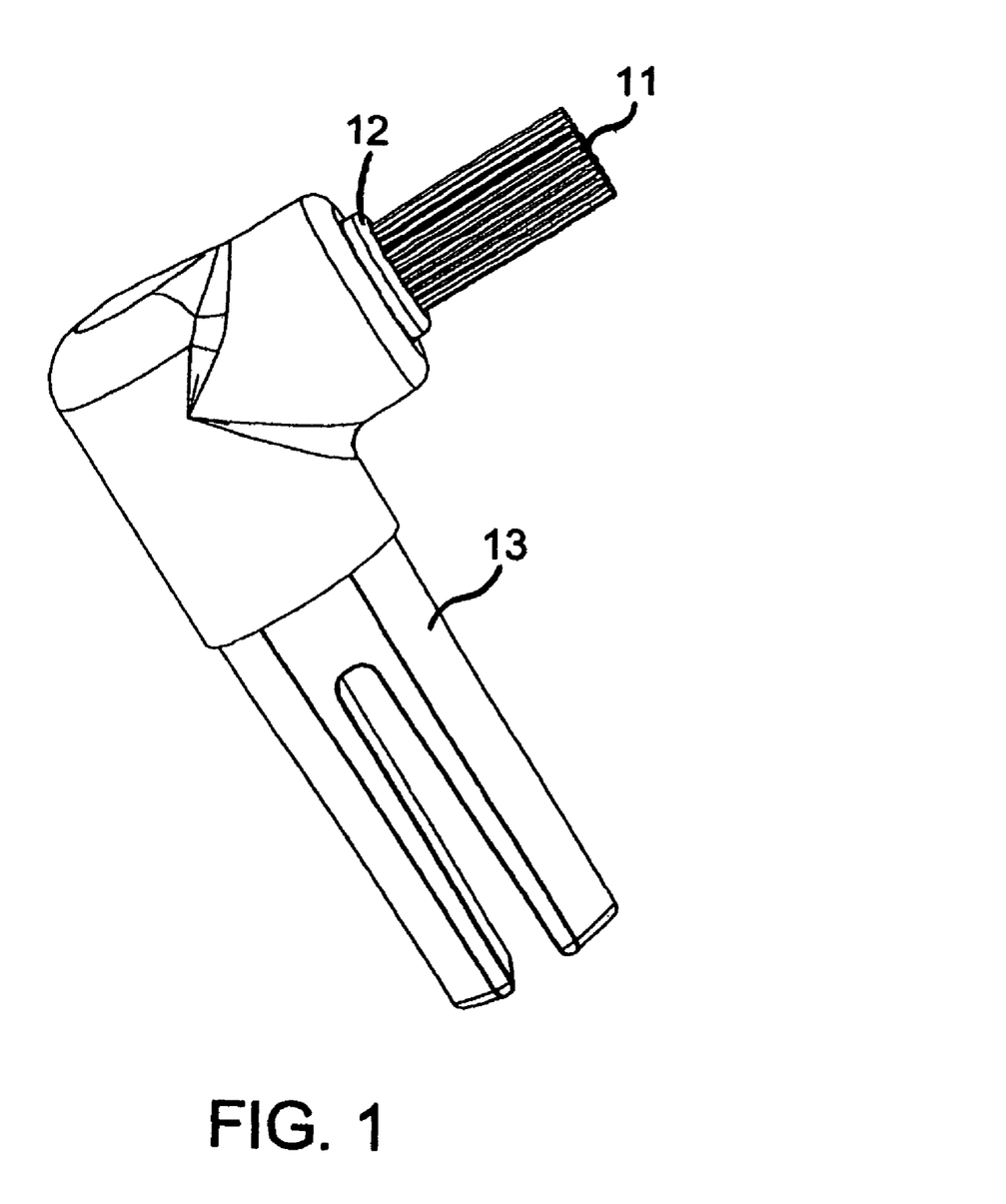
FIG. 1 is a perspective view of a rotating head 13 capable of locking into one of multiple angles. a number of bristles 11 are contained within a plastic shank 12. bristles 11 are of equal length to form a flat, wide surface.

FIG. 1 is a perspective view of a rotating head 13 capable of locking into one of multiple angles. A number of bristles 11 are contained within a plastic shank 12. Bristles 11 are of equal length to form a flat, wide surface.

Figure 2:
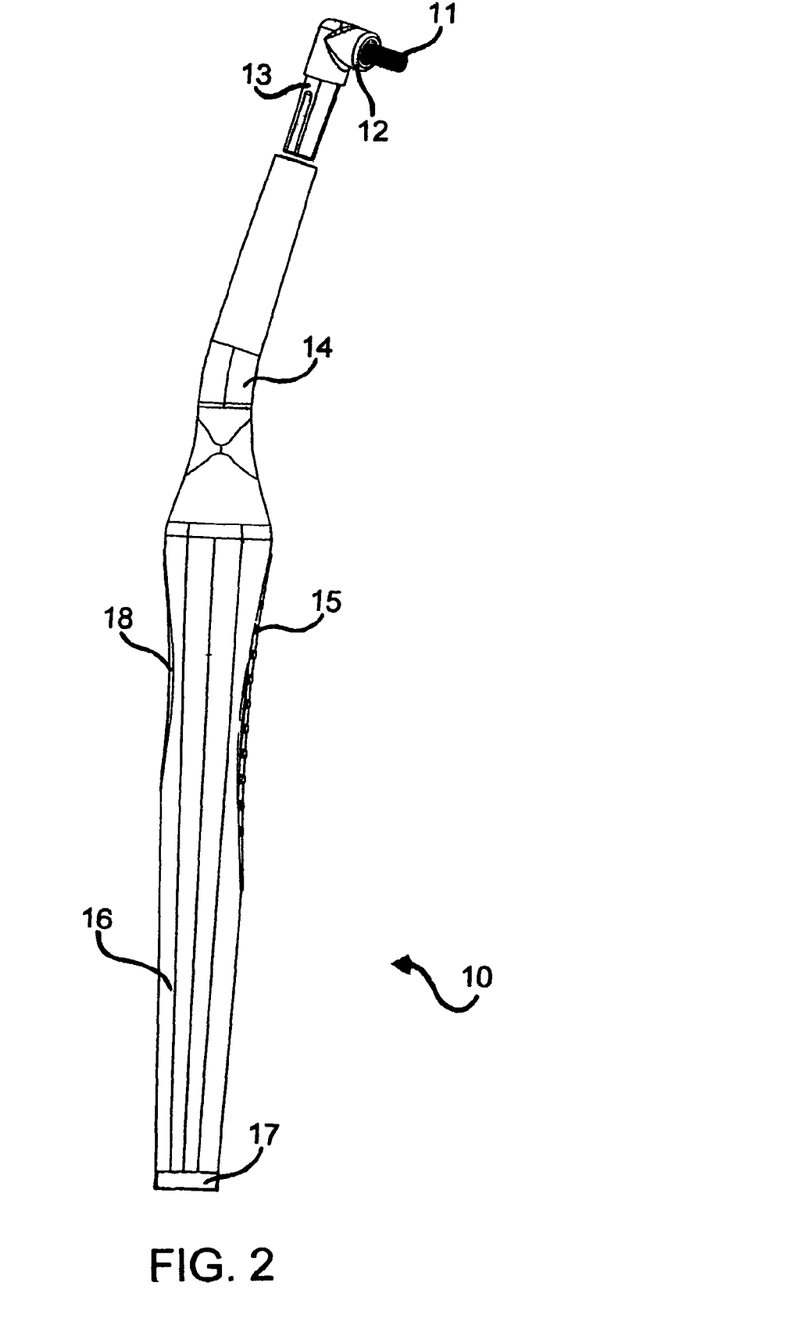
FIG. 2 is a left view of a manual mini multitask brush 10. bristles 11 contained within a plastic shank 12 attach to the rotating head 13 that adjusts and locks into one of multiple angles. angled neck 14 attaches to the handle 16 that presents front soft grip insert 15, back soft grip insert 18 glued to the outer surface to reduce slipping of thumb and finger when wet. removable cap 17 unscrews to reveal storage space.

FIG. 2 is a left view of a manual mini multitask brush 10. Bristles 11 contained within a plastic shank 12 attach to the rotating head 13 that adjusts and locks into one of multiple angles. Angled neck 14 attaches to the handle 16 that presents front soft grip insert 15, back soft grip insert 18 glued to the other surface to reduce slipping of thumb and finger when wet. Removable cap 17 unscrews to reveal storage space.

Figure 3:
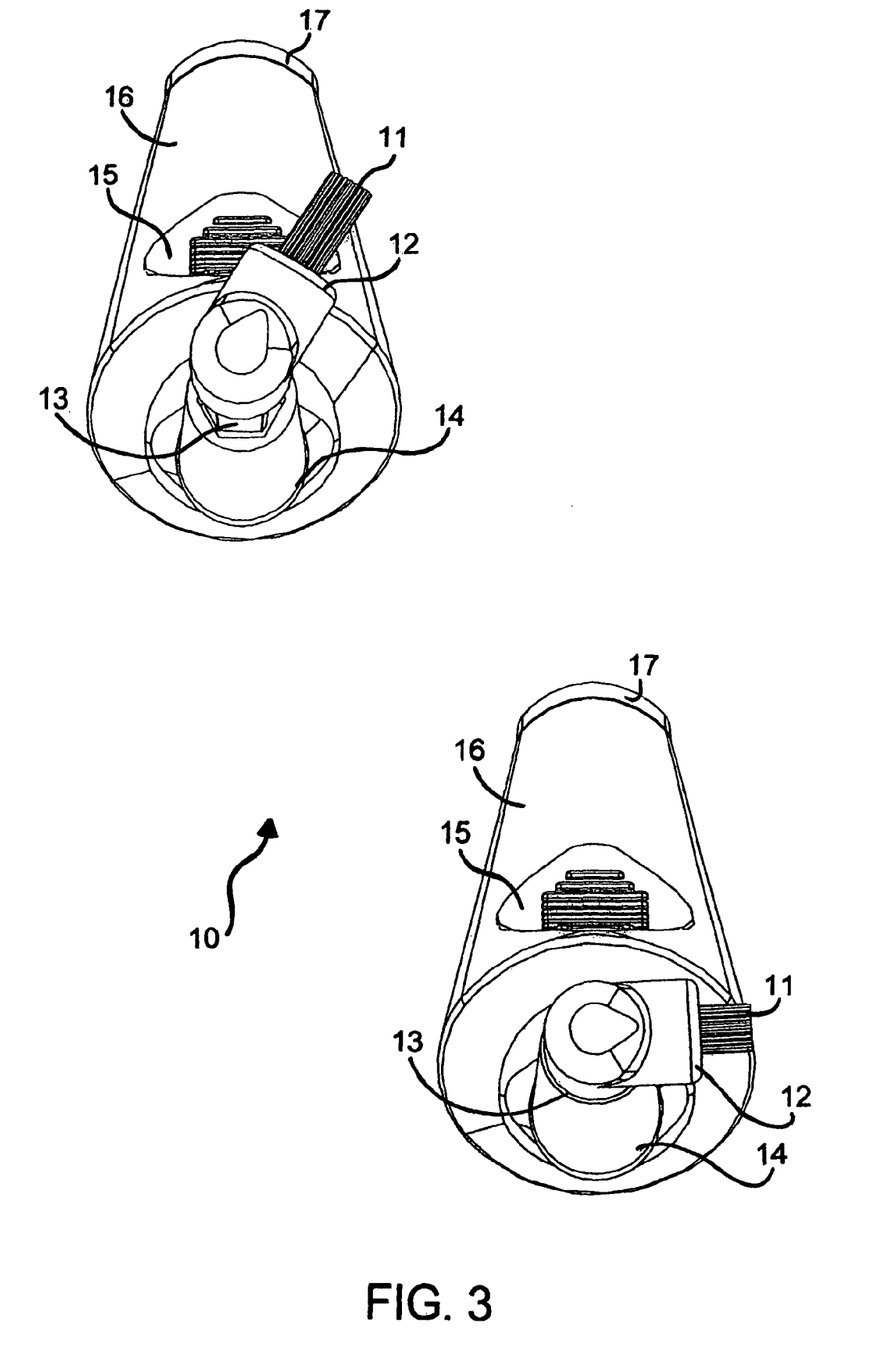
FIG. 3 is a perspective view of a manual mini multitask brush 10 with handle 16 curved for hand comfort. bristles 11 are short, flat and contained within a plastic shank 12 connected to a rotating head 13 that is capable of locking into one of multiple angles. angled neck 14 connects to the handle 16. the handle 16 contains a front soft grip insert 15 and a cap 17 that twists off to reveal a hollow handle for extra brushes.

FIG. 3 is a perspective view of a manual mini multitask brush 10 with handle 16 curved for hand comfort. Bristles 11 are short, flat and contained within a plastic shank 12 connected to a rotating head 13 that connects to an angled neck 14. The handle 16 contains a front soft grip insert 15 and a cap 17 that twists off to reveal a compartment in handle 16 for storage of extra brushes. Two of multiple angles are shown locked into place with rotating head 13.

Figure 4:
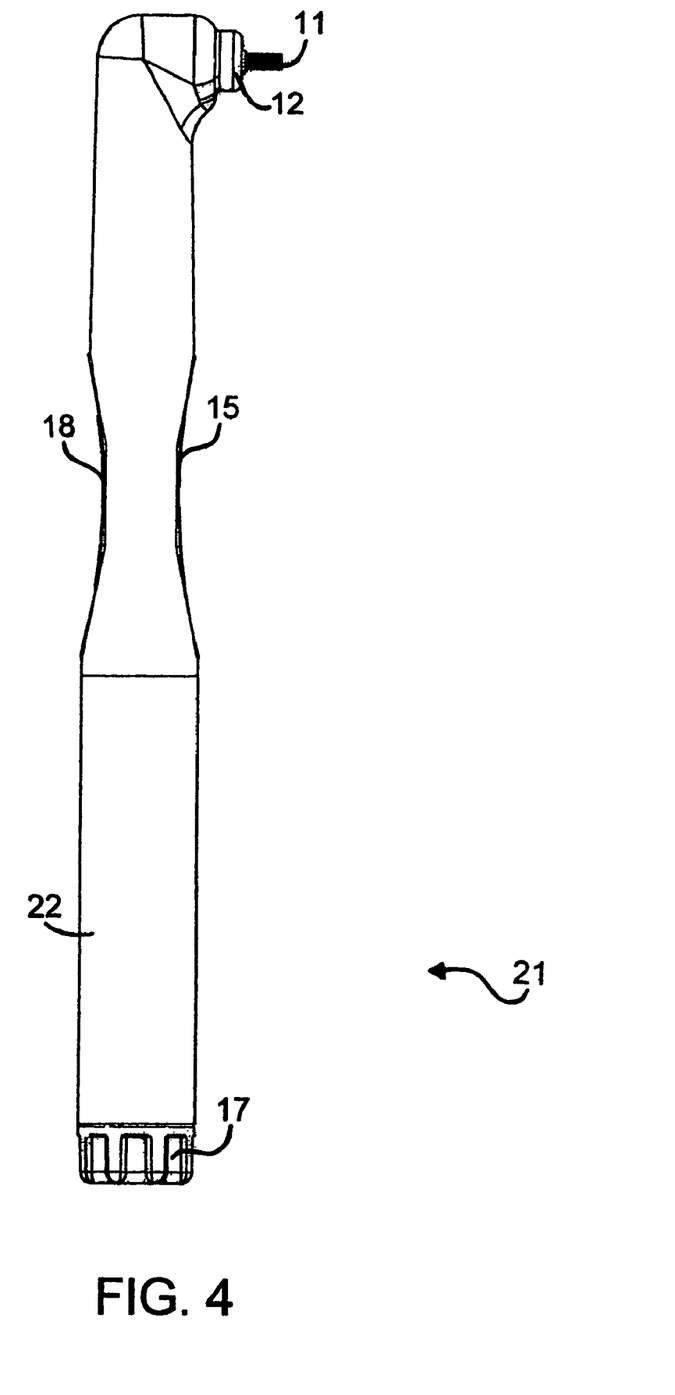
FIG. 4 is a left view of a power mini multitask brush 21 powered by a motor encased within the power mini multitask brush handle 22. the bristles 11 are attached within a plastic shank 12. the power mini multitask brush handle 22 has a front soft grip insert 15 and a back soft grip insert 18 to avoid finger and thumb slipping when wet. the bottom of the handle has a removable cap 17.

FIG. 4 is a left view of a power mini multitask brush 21 powered by a motor encased within the power mini multitask brush handle 22. The bristles 11, are attached within a plastic shank 12. The power mini multitask brush handle 22 has a front soft grip insert 15 and a back soft grip insert 18 to avoid finger and thumb slipping when wet. The bottom of the handle 16 has a removable cap 17.

Figure 5:
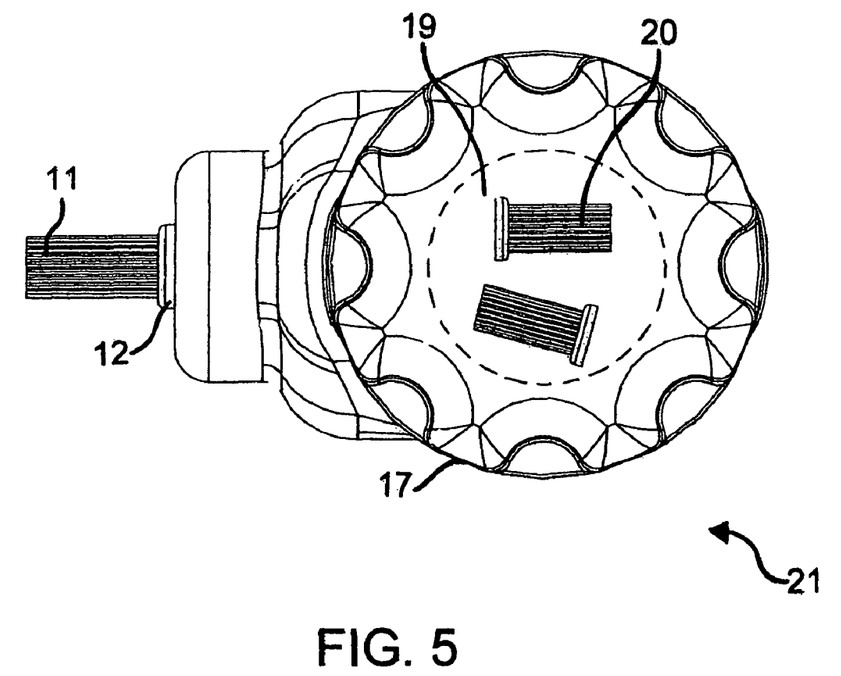
FIG. 5 is a bottom view of a power mini multitask brush 21 showing the removable cap 17 that opens when twisted counter clockwise and tightened when turned clockwise. the removable cap 17 twists off to reveal a hollow space 19 used for storage of additional brushes 20. the bristles 11 are contained within a plastic shank 12.

FIG. 5 is a bottom view of a power mini multitask brush 21 showing the removable cap 17 that opens when twisted counter clockwise and tightened when turned clockwise. The removable cap 17 twists off to reveal a hollow space 19 used for storage of additional brushes 20. The bristles 11 contained within a plastic shank 12 attached within the head is powered by a motor and moves in an agitating or reciprocating articulation.

Figure 6:
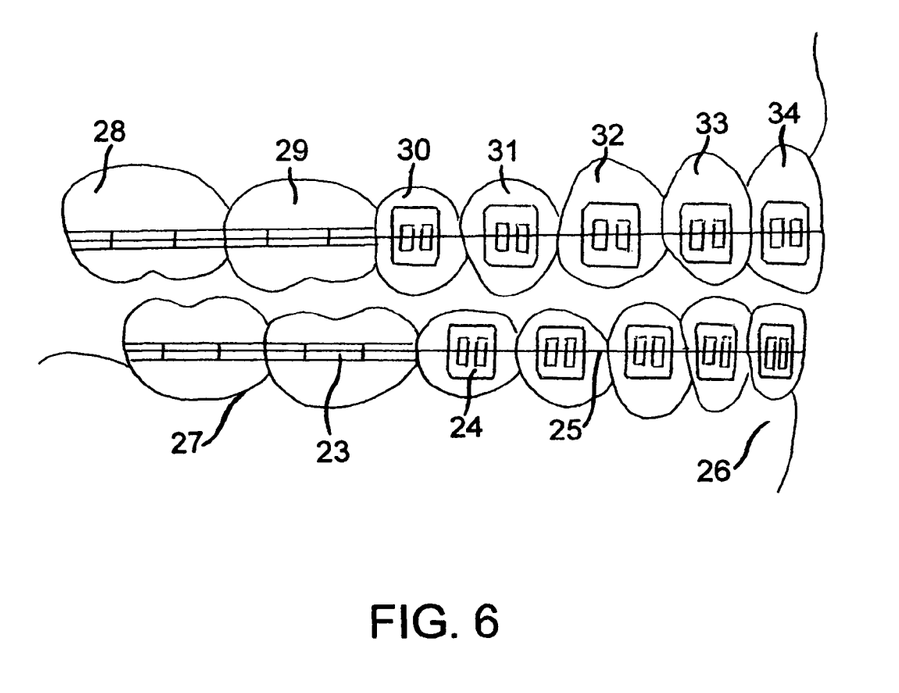
FIG. 6 is a detail view of the first molars 29 and second molars 28 in orthodontic bands 23, first bi-cuspids 31, second bi-cuspids 30, cuspids 32, lateral incisors 33 and central incisors 34 in brackets with an orthodontic arch wire 25 in place. gingiva (gum) 26 surrounds all teeth. the gumline 27 is where the gingiva (gum) 26 meets the teeth. dental plaque rests along the gumline 27 and must be removed to prevent infection of the gingiva (gum) 26. dental plaque also rests along orthodontic brackets 24 and if not removed, will result in decay of teeth.

FIG. 6 which is a detail view of the first molars 29 and second molars 28 in orthodontic bands 23, first bi-cuspids 31 and second bi-cuspids 30, cuspids 32, lateral incisors 33 and central incisors 34 in brackets with an orthodontic arch wire 25 in place. Gingiva (gum) 26 surrounds all teeth. The gumline 27 is where the gingiva (gum) 26 meets the teeth. Dental plaque rests along the gumline 27 and must be removed to prevent infection of the gingiva (gum) 26. Dental plaque also rests along orthodontic brackets 24 and if not removed, will result in decay of teeth.

Figure 7:
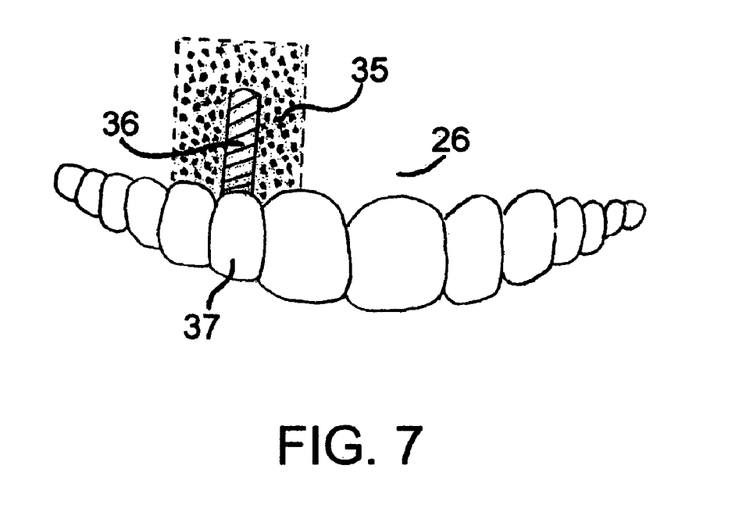
FIG. 7 is a detail view of an implant crown 37. the gingiva (gum) 26 hugs the implant crown 37 tightly making this area hard to remove plaque. an implant 36 cannot be lost to dental decay, but the gingiva (gum) 26 and bone 35 surrounding the implant 36 can become inflamed and infected from bacteria in the plaque causing implant 36 failure.

FIG. 7 which is a detail view of an implant 36 retained crown. Bone 35 surrounds the implant 36 and the gingiva (gum) 26 covers the bone 35. The gingiva (gum) 26 and implant crown 37 fit tightly together making this area hard to remove plaque. An implant 36 cannot be lost to dental decay, but the gingiva (gum) 26 can become inflamed and infected from bacteria in the plaque causing implant 36 failure.

Figure 8:
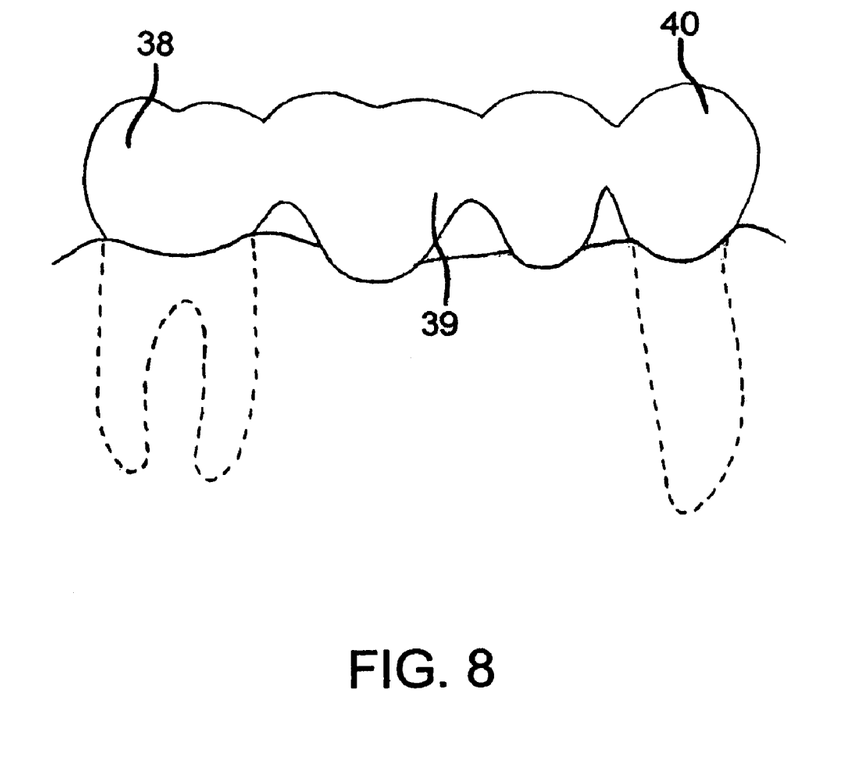
FIG. 8 is a detail view of a dental bridge showing an abutment tooth 38 a pontic 39 and another abutment tooth 40. the abutment tooth has roots, has been crowned and is anchored on both sides of a pontic. the abutment tooth 38 with a root is susceptible to caries if plaque is not removed.

FIG. 8 which is a detail view of a dental bridge showing an abutment tooth 38 on one end of a pontic 39 and another abutment tooth 40 on the other end. The abutment tooth 38 has roots and has been crowned on both sides of missing teeth used to anchor pontic 39 that no longer has roots. The abutment tooth 38 are shaved down to accommodate room for crowns and roots of these abutment tooth 38 are still susceptible to decay if dental plaque is not removed.

Figure 9:
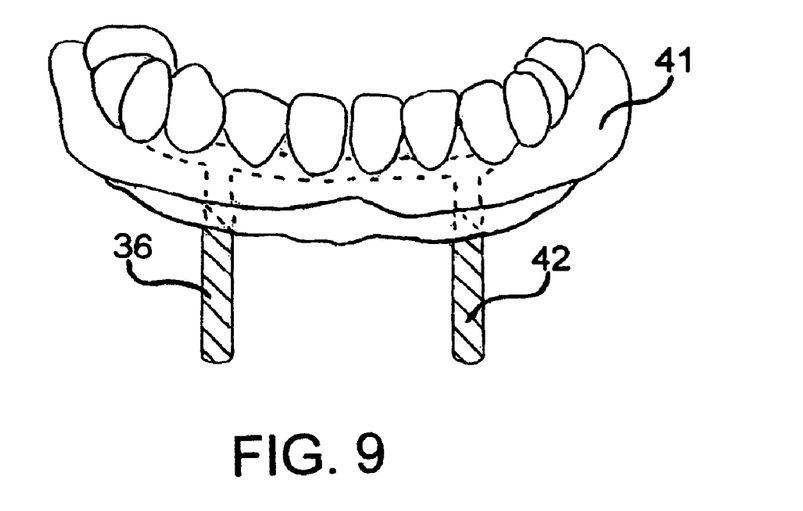
FIG. 9 is a detail view of a removable prosthesis (denture) 41 held in place with an implant 36, and additional implant 42. if dental plaque is not removed around implants, a risk of losing an implant 36 increases due to the bacteria in plaque causing an infection.

FIG. 9 which is a detail view of the removable prosthesis (denture) 41 held in place with additional implant 42. If dental plaque is not removed around additional implant 42, a risk of losing an implant 36 increases due to the bacteria in plaque causing an infection.

Figure 10:
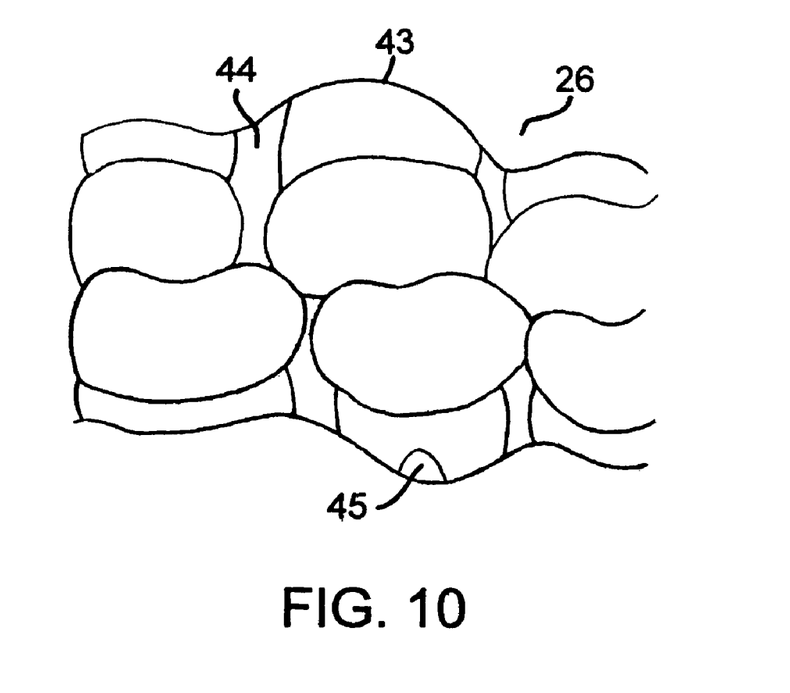

FIG. 10 which is a detail view of the few conditions that the mini multitask brush can help maintain and keep from getting worse. The gingiva (gum) 26 can recede severely with periodontal disease. After periodontal disease is in control, you cannot cure it, but can maintain oral health with the help of a dental professional and excellent home care. Receded gum 43 areas need adequate dental plaque removal to avoid infection and root caries. An embrasure 44 is a wide space in between teeth and develops after periodontal disease due to excessive loss of papilla (gum between teeth) in between teeth. Furcation 45 of the root happens when the gingiva (gum) 26 has receded far enough to expose the space between a root. This is an indentation that is very difficult to clean. Frequent visits to a dental professional and excellent plaque removal are a must.

Figure 11:
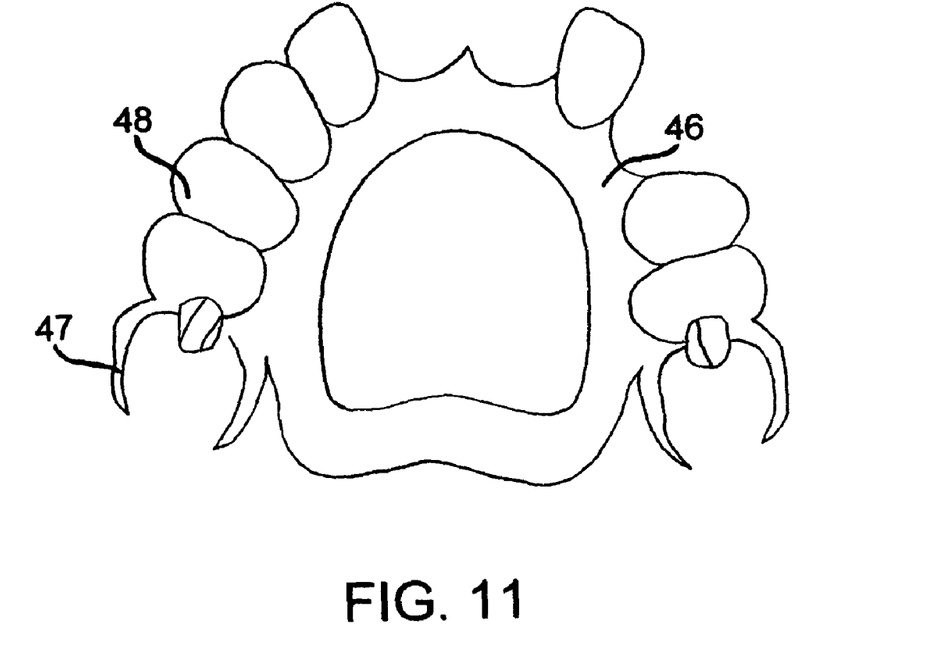
FIG. 11 is a bottom detail view of a partial denture with metal frame 46 and clasps. the metal clasps are delicate and require gentle cleaning. the mini multitask brush can provide gentle and adequate cleaning to a metal clasp 47 and to a partial denture tooth 48.

FIG. 11 which is a bottom detail view of a partial denture with a metal frame 46 and clasp 47. The metal clasp 47 are delicate and require gentle cleaning. The mini multitask brush can provide gentle and adequate cleaning around clasp 47 and a partial denture tooth 48.

Figure 12:
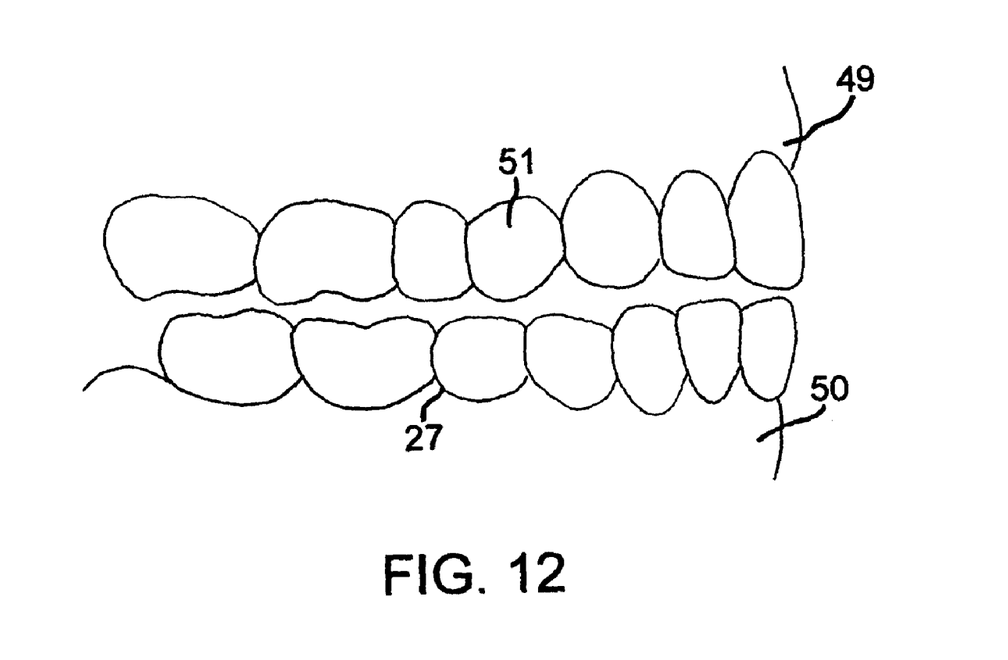
FIG. 12 is a detail view of an upper (maxillary) 49 and lower (mandibular) 50 showing natural healthy teeth 51. the mini multitask brush is excellent for removing plaque on healthy teeth and gums. the stiff, short bristles provide support by not bending and giving way making plaque removal effective along gumline 27.

FIG. 12 which is a detail view of the upper (maxillary 49) and lower (mandibular 50) showing natural healthy teeth 51. The mini multitask brush is excellent for plaque removal along gumline 27 of healthy teeth. The stiff, short brush will provide support by not bending and giving way making plaque removal effective and avoiding infection.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. A brush comprising:
  a) an elongated handle having opposite first and second ends, the handle defining a hollow storage space therein accessible by an opening at the first end thereof with a removable cap being provided for selectively accessing the storage space, the handle further having a pair of grip inserts adjacent the second end on opposite sides of the handle;
  b) an elongated neck extending from the second end of the handle and inclined at an angle with respect to the axis of the handle, the neck further including a receiving portion at the free end thereof opposite the portion adjacent the second end of the handle;
  c) at least one brush member, the brush member including a shank portion provided with a plurality of bristles extending therefrom, the brush further including an insertion portion transversely extending from the shank portion as well as being transverse relative to the bristles, the insertion portion being removably received within the receiving portion in the free end of the neck such that the insertion portion may be fixed at a selected one of a plurality of positions such that the orientation of the bristles of the brush member may be altered relative to the handle; and
  d) wherein additional brush members may be stored in the storage space in the handle.

\* \* \* \* \*